(12) United States Patent
Markman et al.

(10) Patent No.: US 7,407,773 B2
(45) Date of Patent: *Aug. 5, 2008

(54) METHOD FOR CHARACTERIZING A CARBOHYDRATE POLYMER

(75) Inventors: Ofer Markman, Rehovot (IL); Assaf (Assaph) Peretz Oron, Seattle, WA (US); Chana Rothmann-Schertz, Petach Tikva (IL)

(73) Assignee: Procognia, Ltd., Ashdod (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/402,646

(22) Filed: Apr. 11, 2006

(65) Prior Publication Data

US 2007/0092915 A1    Apr. 26, 2007

Related U.S. Application Data

(63) Continuation of application No. 10/275,222, filed as application No. PCT/US00/30402 on Nov. 3, 2000, now Pat. No. 7,132,251.

(51) Int. Cl.
*C12Q 1/34* (2006.01)
(52) U.S. Cl. .................................................. 435/18
(58) Field of Classification Search ............. 536/123.1, 536/123, 124; 435/7.1, 7.72, 18, 72, 174, 435/181
See application file for complete search history.

(56) References Cited

U.S. PATENT DOCUMENTS

| | | | | |
|---|---|---|---|---|
| 5,888,757 | A * | 3/1999 | Kuranda | 435/15 |
| 5,965,457 | A * | 10/1999 | Magnani | 436/518 |
| 6,197,599 | B1 | 3/2001 | Chin et al. | 436/518 |
| 7,056,678 | B1 * | 6/2006 | Markman | 435/7.1 |
| 7,132,251 | B1 * | 11/2006 | Markman et al. | 435/18 |

FOREIGN PATENT DOCUMENTS

| | | |
|---|---|---|
| EP | 0 166 623 A2 | 1/1986 |
| EP | 0 421 972 A2 | 1/1991 |
| WO | WO 93/22678 | 11/1993 |
| WO | WO 93/24503 | 12/1993 |
| WO | WO 97/35201 | 9/1997 |
| WO | WO 99/31267 | 6/1999 |

OTHER PUBLICATIONS

Yamashita K. Characteristics of Asparagine Linked Sugar Chains . . . Biochemistry vol. 29, 3030-3039, 1990.*
Andy et al. *J. Biol. Chem.*, 259(20):12844-12849 (1984).
Deng et al. *J. Biol. Chem.*, 269(13):9533-9538 (1994).
Galanina et al. *Tumor Biol.*, 19(Suppl. 1):79-87 (1998).
Goodarazi et al. *Glicoconjugate J.*, Abstract only, 14(4):493-496 (1997).
Hutchinson, A. *Anal Biochem.* 220(2):303-307 (1994).
Knels et al. *J. Comp. Physiol. B*, 159: 629-639 (1989).
Laidler et al. *Int. J. Biochem. Cell Biol.*, 29(3):475-483 (1997).
Magnani, J. *Anal. Biochem.*, 150(1):13-17 (1985).
Rahman et al. *Microbial Pathogenesis*, 24:299-308 (1998).
Smith et al. *J. Biol. Chem.*, 262(25):12040-12047 (1987).
Yamashita et al. *Biochem.*, 27(15):5565-5573 (1988).
Yamashita et al. *Biochem.*, 29(12):3030-3039 (1990).

* cited by examiner

*Primary Examiner*—Ralph Gitomer
(74) *Attorney, Agent, or Firm*—Ivor R. Elrifi; David E. Johnson; Mintz Levin Cohn Ferris Glovsky and Popeo, PC

(57) ABSTRACT

Disclosed is a method for characterizing carbohydrate polymer by identifying at least two binding agents that bind to the carbohydrate polymer. Binding is preferably determined by contacting the carbohydrate polymer with substrate that contains a plurality of first saccharide-binding agents affixed at predetermined locations on the substrate. The carbohydrate polymer is allowed to contact the substrate under conditions that allow for formation of a first complex between the first saccharide-binding agent and the carbohydrate polymer. A second saccharide-binding agent, which preferably includes a label, is also contacted with the carbohydrate polymer under conditions that allow for formation of a second complex between the second binding agent and the first complex. Identification of the first and second binding agent allows for characterization of the polysaccharide.

37 Claims, 4 Drawing Sheets

METHOD FOR CHARACTERIZING A CARBOHYDRATE POLYMER

RELATED APPLICATIONS

This application is a continuation of Ser. No.10/275,222 filed Sep. 9, 2003, now U.S. Pat. No. 7,132,251, which is a 371 US National filing of PCT/US00/30402, filed Nov. 3, 2000, which claims priority to Israel Application 00/00256, filed Apr. 4, 2000.

FIELD OF THE INVENTION

The invention relates generally to a method for analyzing molecules containing polysaccharides and more particularly to a method for analyzing polysaccharides based using saccharide-binding agents such as lectins.

BACKGROUND OF THE INVENTION

Polysaccharides are polymers that include monosaccharide (sugar) units connected to each other via glycosidic bonds. These polymers have a structure that can be described in terms of the linear sequence of the monosaccharide subunits, which is known as the two-dimensional structure of the polysaccharide. Polysaccharides can also be described in terms of the structures formed in space by their component monosaccharide subunits.

A chain of monosaccharides that form a polysaccharide has two dissimilar ends. One end contains an aldehyde group and is known as the reducing end. The other end is known as the non-reducing end. A polysaccharide chain may also be connected to any of the C1, C2, C3, C4, or C6 atom if the sugar unit it is connected to is a hexose. In addition, a given monosaccharide may be linked to more than two different monosaccharides. Moreover, the connection to the C1 atom may be in either the $\alpha$ or $\beta$ configuration. Thus, both the two-dimensional and three-dimensional structure of the carbohydrate polymer can be highly complex.

The structural determination of polysaccharides is of fundamental importance for the development of glycobiology. Research in glycobiology relates to subjects as diverse as the identification and characterization of antibiotic agents that affect bacterial cell wall synthesis, blood glycans, growth factor and cell surface receptor structures involved in viral disease, and autoimmune diseases such as insulin dependent diabetes, rheumatoid arthritis, and abnormal cell growth, such as that which occurs in cancer.

Polysaccharides have also been used in the development of biomaterials for contact lenses, artificial skin, and prosthetic devices. Furthermore, polysaccharides are used in a number of non-medical fields, such as the paper industry. Additionally, of course, the food and drug industry uses large amounts of various polysaccharides and oligosaccharides.

In all of the above fields, there is a need for improved saccharide analysis technologies. Saccharide analysis information is useful in, e.g., for quality control, structure determination in research, and for conducting structure-function analyses.

The structural complexity of polysaccharides has hindered their analysis. For example, saccharides are believed to be synthesized in a template-independent mechanism. In the absence of structural information, the researcher must therefore assume that the building units are selected from any of the saccharide units known today. In addition, these units may have been modified, during synthesis, e.g., by the addition of sulfate groups.

Second, saccharide can be connected at any of the carbon moieties, e.g., a the C1, C2, C3, C4, or C6 atom if the sugar unit it is connected to is a hexose. Moreover, the connection to the C1 atom may be in either $\alpha$ or $\beta$ configuration.

Third, saccharides may be branched, which further complicates their structure and the number of possible structures that have an identical number and kind of sugar units.

A fourth difficulty is presented by the fact that the difference in structure between many sugars is minute, as a sugar unit may differ from another merely by the position of the hydroxyl groups (epimers).

The use of a plurality of such saccharide-binding agents, whether fixed to the substrate and/or employed as the second (soluble) saccbaride-binding agent, characterizes the carbohydrate polymer of interest by providing a "fingerprint" of the saccharide. Such a fingerprint can then be analyzed in order to obtain more information about the carbohydrate polymer. Unfortunately, the process of characterization and interpretation of the data for carbohydrate polymer fingerprints is far more complex than for other biological polymers, such as DNA for example. Unlike binding DNA probes to a sample of DNA for the purpose of characterization, the carbohydrate polymer fingerprint is not necessarily a direct indication of the components of the carbohydrate polymer itself. DNA probe binding provides relatively direct information about the sequence of the DNA sample itself, since under the proper conditions, recognition and binding of a probe to DNA is a fairly straightforward rocess. Thus, a DNA "fingerprint" which is obtained from probe binding can yield direct information about the actual sequence of DNA in the sample.

By contrast, binding of agents to carbohydrate polymers is not nearly so traightforward. As previously described, even the two-dimensional structure (sequence) of carbohydrate polymers is more complex than that of DNA, since carbohydrate polymers can be branched. These branches clearly affect the three-dimensional structure of the polymer, and hence the structure of the recognition site for the binding agent. In addition, recognition of binding epitopes on carbohydrate polymers by the binding agents may be affected by the "neighborhood" of the portion of the molecule which is surrounding the epitope. Thus, the analysis of such "fingerprint" data for the binding of agents to the carbohydrate polymer of interest is clearly more difficult than for DNA probe binding, for example.

A useful solution to this problem would enable the fingerprint data to be analyzed in order to characterize the carbohydrate polymer. Such an analysis would need to transform the raw data, obtained from the previously described process of incubating saccharide-binding agents with the carbohydrate polymer, into a fingerprint which would itself contain information. The fingerprint would also need to be standardized for comparison across different sets of experimental conditions and for different types of saccharide-binding agents. Unfortunately, such a solution is not currently available.

In spite of these difficulties, a number of methods for the structural analysis of saccharides have been developed. For example, PCT Application No. WO 93/24503 discloses a method wherein monosaccharide units are sequentially removed from the reducing end of an oligosaccharide by converting the monosaccharide at the reducing end to its keto- or aldehyde form, and then cleaving the glycosidic bond between the monosaccharide and the next monosaccharide in the oligosaccharide chain by using hydrazine. The free monosaccharides are separated from the oligosaccharide chain and identified by chromatographic methods. The process is then repeated until all monosaccharides have been cleaved.

PCT Application No. WO 93/22678 discloses a method of sequencing an unknown oligosaccharide by making assumptions upon the basic structure thereof, and then choosing from a number of sequencing tools (such as glycosidases) one which is predicted to give the highest amount of structural information. This method requires some basic information as to the oligosaccharide structure (usually the monosaccharide composition). The method also illustrates the fact that reactions with sequencing reagents are expensive and time-consuming, and therefore there is a need for a method that reduces these expenses.

PCT Application No. WO 93/22678 discloses a method for detecting molecules by probing a monolithic array of probes, such as oligodeoxynucleotides, immobilized on a VLSI chip. This publication teaches that a large number of probes can be bound to an immobilized surface, and the reaction thereof with an analyte detected by a variety of methods, using logic circuitry on the VLSI chip.

European Patent Application No. EP 421,972 discloses a method for sequencing oligosaccharides by labeling one end thereof, dividing the labeled oligosaccharide into aliquots, and treating each aliquot with a different reagent mix (e.g. of glycosidases), pooling the different reaction mixes, and then analyzing the reaction products, using chromatographic methods. This method is useful for N-linked glycans only, as they have a common structure at the point where the saccharide chain is linked to the protein. O-linked glycans are more varied, and the method has as yet not been adapted for such oligosaccharides with greater variability in their basic structure.

There is therefore a need for a system and method for characterizing polysaccharides using an accurate, high throughput method for identifying agents that bind to the polysaccharide.

SUMMARY OF THE INVENTION

The invention is based in part on the discovery of a method for quickly and accurately identifying agents that bind a given carbohydrate polymer. Also provided by the invention is a method for generating a fingerprint of a carbohydrate polymer that is based on its pattern of binding to saccharide-binding agents.

In one aspect, the invention features a method for characterizing a carbohydrate polymer. The carbohydrate polymer is contacted with a surface that includes at least one first saccharide-binding agent attached to a predetermined location on the surface under conditions allowing for the formation of a first complex between the first saccharide-binding agent and the carbohydrate polymer. The surface is then contacted with at least one second saccharide-binding agent under conditions allowing for formation of a second complex between the first complex and the second saccharide-binding agent. The first saccharide-binding agent and second saccharide-binding agent are then identified, thereby characterizing the carbohydrate polymer.

Also provided by the invention is a method of generating a fingerprint of a carbohydrate polymer by contacting a carbohydrate polymer with a first saccharide-binding agent, determining whether the carbohydrate polymer binds to the saccharide-binding reagent, contacting the carbohydrate polymer with a second saccharide-binding agent, and determining whether the carbohydrate polymer binds to the second saccharide-binding reagent. Identification of the first and second saccharide-binding agent is used to generate a fingerprint of the carbohydrate polymer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1A:
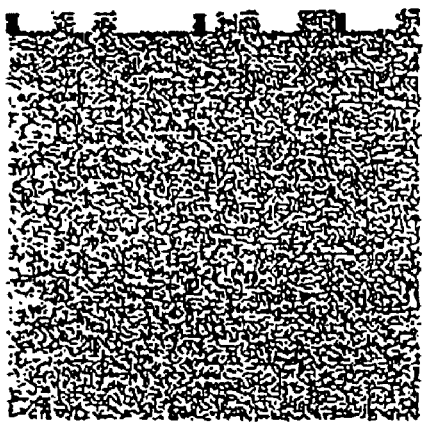
FIG. 1 is an illustration of the Glycomolecule identity (GMID) cards obtained for pasteurized goat's milk (A and B), non-pasteurized goat's milk (C and D) and bovine milk
Figure 1B:
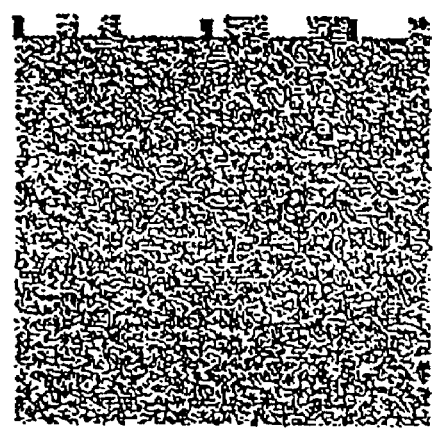
Figure 1C:
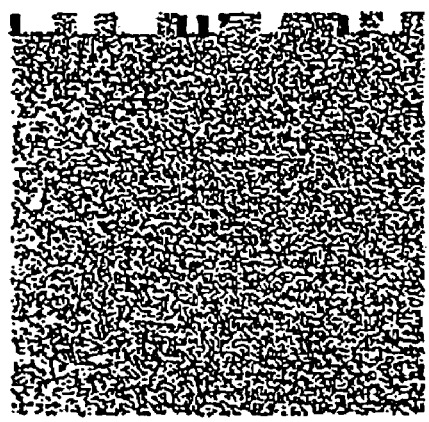
Figure 1D:
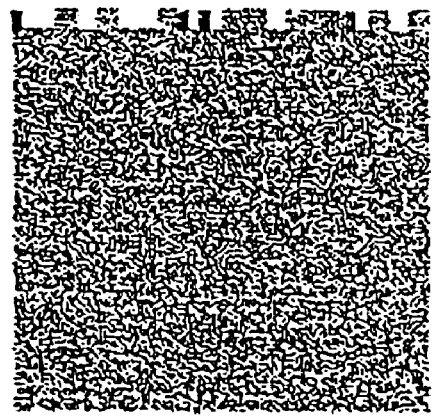
Figure 1E:
Figure 2A:
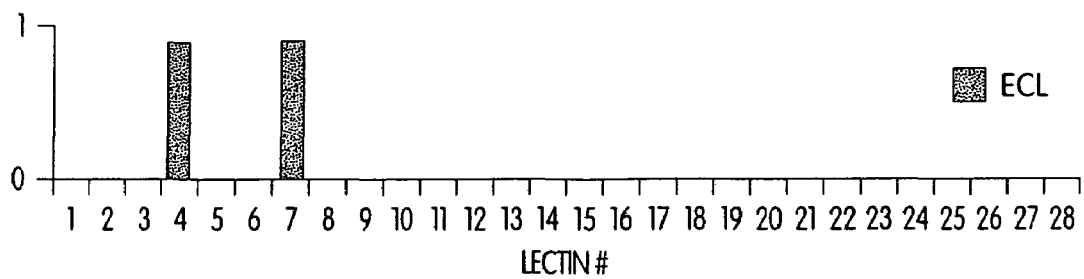
FIG. 2 is a reproduction of the GMID cards obtained for various lipopolysaccharide samples. Cards A to E correspond to LPS# 1, 7, 10, 15 and 16 respectively.
Figure 2B:
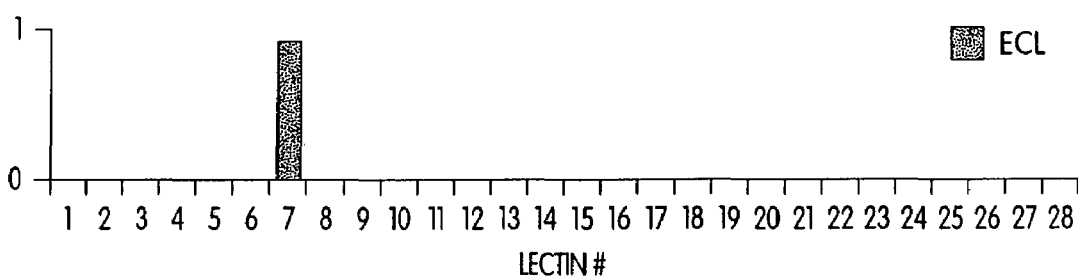
Figure 2C:
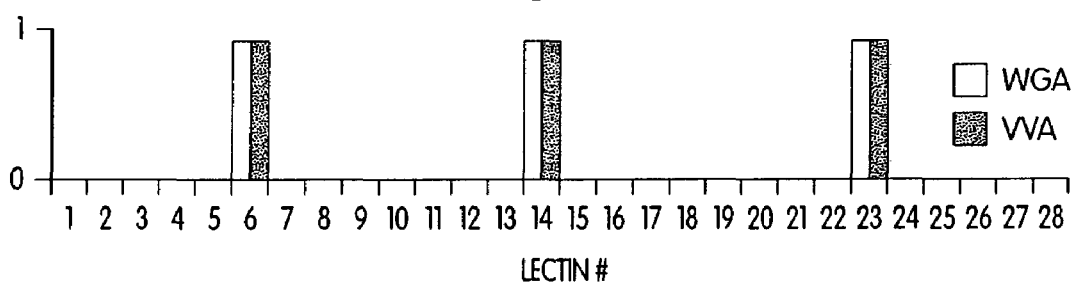
Figure 2D:
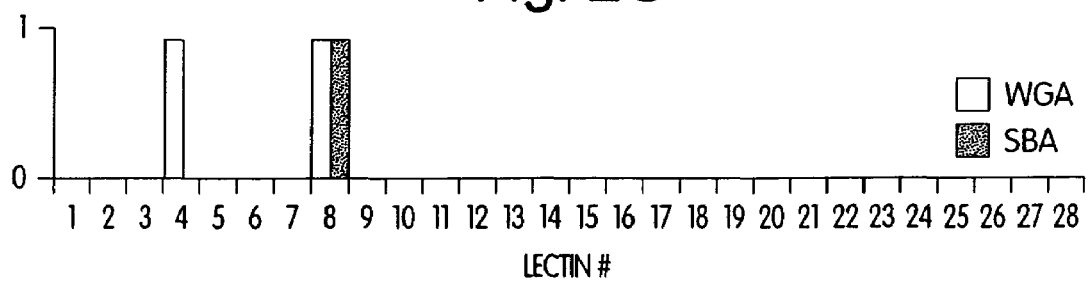
Figure 2E:
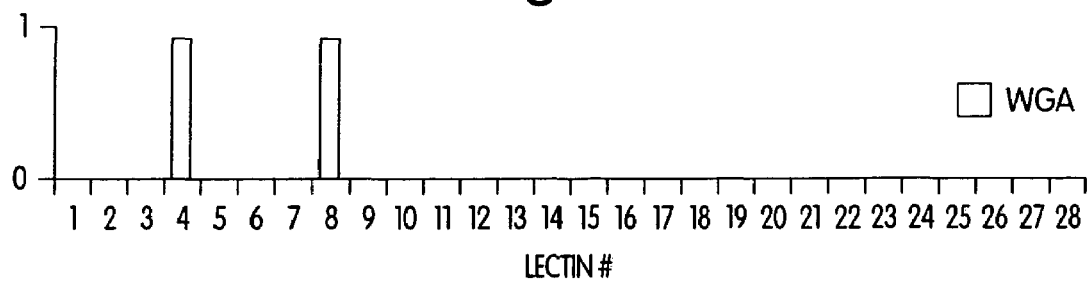

Provided by the invention is a method for characterizing a carbohydrate polymer by systemically assembling a representation of information that describes the binding status of the carbohydrate polymer with respect to saccharide-binding agents.

To assess binding status, the carbohydrate polymer is added to a surface that includes at least one saccharide-binding agent attached to a predetermined location on the surface. The carbohydrate polymer is incubated with the surface under conditions allowing for the formation of a complex between the first saccharide-binding agent and the carbohydrate polymer. The surface can then be washed if desired to remove unbound carbohydrate polymer. The surface is then contacted with a second saccharide-binding agent under conditions allowing for formation of a second complex between the first complex and the second saccharide-binding agent. The second agent preferably carries a detectable label to allow for detection of the second complex. Detection of the second complex at a location on the substrate corresponding to the location of a predetermined binding-agent allows for the identification of the first and second binding agents as agents that bind to the carbohydrate polymer. Detecting the first and second-binding agents provides structural information about the carbohydrate polymer.

While the method has been described by first contacting the carbohydrate polymer with the surface and then adding a detectable label, it is understood that this order is not obligatory. Thus, in some embodiments, the second agent is mixed with the carbohydrate polymer, and this complex is added to the surface.

In some embodiments, a plurality of saccharide-binding agents are attached to the surface. Similarly, a plurality of second detectable saccharide-binding agents may be used. In preferred embodiments, a plurality of both first and second saccharide-binding agents are used.

Thus, in various embodiments, at least, 5, 10, 15, 25, 30, or 50 or more first saccharide-binding agents are attached to the surface. Preferably, each the first saccharide-binding agents are attached at spatially distinct regions of the substrate.

In other embodiments, at least 5, 10, 15, 25, 30, or 50 of more second-saccharide binding agents are used. Preferably, each of the second-saccharide have attached thereto distinguishable labels, i.e., labels that distinguish one-second saccharide-binding agent from another second saccharide-binding agent.

As used herein, a "carbohydrate polymer" includes any molecule with a polysaccharide component. Examples include polysaccharide, a glycoprotein, and glycolipid. While a carbohydrate polymer includes any saccharide molecule containing two or more linked monosaccharide residues, it is understood that in most embodiments, the carbohydrate polymer will include 10, 25, 50, 1000, or 10,000 or more monosaccharide units. If desired, the carbohydrate polymer can be added to the surface after digestion with a saccharide-cleaving agent. Alternatively, the carbohydrate polymer can be added to the surface, allowed to bind to a first saccharide-binding agent attached to the surface, and then digested with a saccharide-cleaving agent.

In general, any agent that binds to a polysaccharide can be used as the first or second saccharide-binding agent. As is known in the art, a number of agents that bind to saccharides have been described. One class of agents is the lectins. Many of these proteins bind specifically to a certain short oligosaccharide sequence. A second class of agents is an antibody that specifically recognize saccharide structures. A third class of saccharide-binding agents is proteins that bind to carbohydrate residues. For example, glycosidases are enzymes that cleave glycosidic bonds within the saccharide chain. Some glycosidases may recognize certain oligosaccharide sequences specifically. Another class of enzymes is glycosyltransferases, which cleave the saccharide chain, but further transfer a sugar unit to one of the newly created ends.

For the purpose of this application, the term "lectin" also encompasses saccharide-binding proteins from animal species (e.g. "mammalian lectins"). Thus, carbohydrate polymers, like DNA or proteins, clearly have an important biological function which should be studied in greater detail.

A saccharide-binding agent is preferably an essentially sequence-specific agent. As used herein, "essentially sequence-specific agent" means an agent capable of binding to a saccharide. The binding is usually sequence-specific, i.e., the agent will bind a certain sequence of monosaccharide units only. However, this sequence specificity may not be absolute, as the agent may bind other related sequences (such as monosaccharide sequences wherein one or more of the saccharides have been deleted, changed or inserted). The agent ay also bind, in addition to a given sequence of monosaccharides, one or more unrelated sequences, or monosaccharides.

The essentially sequence-specific agent is usually a protein, such as a lectin, a saccharide-specific antibody or a glycosidase or glycosyltransferase.

Examples of saccharide-binding agents lectins include lectins isolated from the following plants: *Conavalia ensiformis, Anguilla anguilla, Triticum vulgaris, Datura tramoniuim, Galanthus nivalis, Maackia amurensis, Arachis hypogaea, Sambucus nigra, Erythrina cristagalli, Lens culinaris, Glycine max, Phaseolus vulgaris, Allomyrina dichotoma, Dolichos biflorus, Lotus tetragonolobus, Ulex europaeus,* and *Ricinus communis*.

Other biologically active carbohydrate-binding compounds include cytokines, chemokines and growth factors. These compounds are also considered to be lectins for this patent application.

Examples of glycosidases include α-Galactosidase, β-Galactosidase, N-acetylhexosaminidase, α-Mannosidase, β-Mannosidase, α-Fucosidase, and the like. Some of these enzymes may, depending upon the source of isolation thereof, have a different specificity. The above enzymes are commercially available, e.g., from Oxford Glycosystems Ltd., Abingdon, OX14 1RG, UK, Sigma Chemical Co., St. Lois, Mo., USA, or Pierce, POB. 117, Rockford, 61105 USA.

The saccharide-binding agent can also be a cleaving agent. A "cleaving agent" is an essentially sequence-specific agent that cleaves the saccharide chain at its recognition sequence. Typical cleaving agents are glycosidases, including exo- and endoglycosidases, and glycosyltransferases. However, chemical reagents capable of cleaving a glycosidic bond may also serve as cleaving agents, as long as they are essentially sequence-specific. The term "cleaving agent" or "cleavage agent" is within the context of this specification synonymous with the term "essentially sequence-specific agent capable of cleaving".

The cleaving agent may act at a recognition sequence. A "recognition sequence" as used herein is the sequence of monosaccharides recognized by an essentially sequence-specific agent. Recognition sequences usually comprise 2-4 monosaccharide units. An example of a recognition sequence is Galβ1-3 GalNAc, which is recognized by a lectin purified from *Arachis hypogaea*. Single monosaccharides, when specifically recognized by an essentially sequence-specific agent, may, for the purpose of this disclosure, be defined as recognition sequences.

The reaction conditions for the various essentially sequence-specific agents are known in the art. Alternatively, the skilled person may easily perform a series of tests with each essentially sequence-specific agent, measuring the binding activity thereof, under various reaction conditions. Advantageously, knowledge of reaction conditions under which a certain essentially sequence-specific agent will react, and of conditions under which it remain inactive, may be used to control reactions in which several essentially sequence-specific reagents are present. For example, the second and third sequence-specific reagents may be added to the reaction simultaneously, but via a change in reaction conditions, only the second essentially sequence-specific agent may be allowed to be active. A further change in reaction conditions may then be selected in order to inactivate the second essentially sequence-specific agent and activate the third essentially sequence-specific agent. Some illustrative examples of reaction conditions are listed in the Table 1 below. In addition to the pH and temperature data listed in Table 1, other factor, e.g. the presence of metals such as Zn, or salts of cations such as Mn, Ca, Na, such as sodium chloride salt, may be investigated to find optimum reaction conditions or conditions under which certain essentially sequence-specific agent will be active, while others are inactive.

TABLE 1

Reaction conditions for some essentially sequence-specific agents

| codes for condition sets | Condition serial number | pH | Temp (C.) | Enzyme(s) |
|---|---|---|---|---|
| ♣♥ | 1 | 3.5 | 30 | Jackbean β-galactosidase |
| ♥ | 2 | 5.0 | 37 | Endo a-N Acetylgalactosidase α 1,2 Fucosidase β1,2 galactosidase |
| ♣ ♠ | 3 | 5.0 | 25 | Bovine kidney α Fucosidase |
| ♥♠ | 4 | 7.2 | 25 | Coffee bean α galactosidase |

TABLE 1-continued

Reaction conditions for some essentially sequence-specific agents

| codes for condition sets | Condition serial number | pH | Temp (C.) | Enzyme(s) |
|---|---|---|---|---|
| ♣♥♠ | 5 | 5.8 | 55 | *B. Fragilis* Endo β-galactosidase |
|  | 6 | 6.2 | 25 | Chicken egg lysozyme |
|  | 7 | 4.3 | 37 | Bovine testes β 1–3,4,6, Galactosidase |
|  | from Biodiversa | 2–9.5 | 50 | Gly 001–02 |
|  | from Biodiversa | 3.0–8.0 | 50 | Gly 001–04 |
|  | from Biodiversa | 2–11 | 50 | Gly 001–06 |

Symbols represent enzyme groups which are separable by external conditions. Diversa Corp. produces Thermophilic Endo/Exo glycosidases with a wide variety of activity in various pH and Temperatures The first saccharine-binding agent may be immobilized using any art-recognized method. For example, immobilization may utilize functional groups of the protein, such as amino, carboxy, hydroxyl, or thiol groups. For instance, a glass support may be functionalized with an epode group by reaction with epoxy silane, as described in the above PCT publication. The epode group reacts with amino groups such as the free ε-amino groups of lysine residues. Another mechanism consists in covering a surface with electrometer materials such as gold, as also described in the PCT publication. As such materials form stable conjugates with thiol groups, a protein may be linked to such materials directly by free thiol groups of cysteine residues. Alternatively, thiol groups may be introduced into the protein by conventional chemistry, or by reaction with a molecule that contains: one or more thiol groups and a group reacting with free amino groups, such as the N-hydroxyl succinimidyl ester of cysteine. Also thiol-cleavable cross-linkers, such as dithiobis(succinimidyl propionate) may be reacted with amino groups of a protein. A reduction with sulfhydryl agent will then expose free thiol groups of the cross-linker.

The label attached to the second detectable label can be any label that is detected, or is capable of being detected. Examples of suitable labels include, e.g., chromogenic label, a radiolabel, a fluorescent label, and a biotinylated label. Thus, the label can be, e.g. colored lectins, fluorescent lectins, biotin-labeled lectins, fluorescent labels, fluorescent antibodies, biotin-labeled antibodies, and enzyme-labeled antibodies. In preferred embodiments, the label is a chromogenic label. The term "chromogenic binding agent" as used herein includes all agents that bind to saccharides and which have a distinct color or otherwise detectable marker, such that following binding to a saccharide, the saccharide acquires the color or other marker. In addition to chemical structures having intrinsic, readily-observable colors in the visible range, other markers used include fluorescent groups, biotin tags, enzymes (that may be used in a reaction that results in the formation of a colored product), magnetic and isotopic markers, and so on. The foregoing list of detectable markers is for illustrative purposes only, and is in no way intended to be limiting or exhaustive. In a similar vein, the term "color" as used herein (e.g. in the context of step (e) of the above described method) also includes any detectable marker.

The label may be attached to the second saccharide-binding agent using methods known in the art. Labels include any detectable group attached to the saccharide or essentially sequence-specific agent that does not interfere with its function. Labels may be enzymes, such as peroxidase and phosphatase. In principle, also enzymes such as glucose oxidase and β-galactosidase could be used. It must then be taken into account that the saccharide may be modified if it contains the monosaccharide units that react with such enzymes. Further labels that may be used include fluorescent labels, such as Fluorescein, Texas Red, Lucifer Yellow, Rhodamine, Nilered, tetramethyl-rhodamine-5-isothiocyanate, 1,6-diphenyl-1,3,5-hexatriene, cis-Parinaric acid, Phycoerythrin, Allophycocyanin, 4',6-diamidino-2-phenylindole (DAPI), Hoechst 33258, 2-aminobenzamide, and the like. Further labels include electron dense metals, such as gold, ligands, haptens, such as biotin, radioactive labels.

The second saccharide-binding agent can be detected using enzymatic labels. The detection of enzymatic labels is well known in the art of ELISA and other techniques where enzymatic detection is routinely used. The enzymes are available commercially, e.g., from companies such as Pierce.

In some embodiments, the label is detected using fluorescent labels. Fluorescent labels require an excitation at a certain wavelength and detection at a different wavelength. The methods for fluorescent detection are well known in the art and have been published in many articles and textbooks. A selection of publications on this topic can be found at p. 0-124 to 0-126 in the 1994 catalog of Pierce. Fluorescent labels are commercially available from Companies such as SIGMA, or the above-noted Pierce catalog.

The second saccharide-binding agent may itself contain a carbohydrate moiety and/or protein. Coupling labels to proteins and sugars are techniques well known in the art. For instance, commercial kits for labeling saccharides with fluorescent or radioactive labels are available from Oxford Glycosystems, Abingdon, UK. Reagents and instructions for their use for labeling proteins are available from the above-noted Pierce catalog.

Coupling is usually carried out by using functional groups, such as hydroxyl, aldehyde, keto, amino, sulfhydryl, carboxylic acid, or the like groups. A number of labels, such as fluorescent labels, are commercially available that react with these groups. In addition, bifunctional cross-linkers that react with the label on one side and with the protein or saccharide on the other may be employed. The use of cross-inkers may be advantageous in order to avoid loss of function of the protein or saccharide.

The label can be detected using methods known in the art. Some detection methods are described in the above-noted; WO 93/22678, the disclosure of which is incorporated herein in its entirety. Particularly suitable for the method of the present invention is the CCD detector method, described in the publication. This method may be used in combination with labels that absorb light at certain frequencies, and so block the path of a test light source to the VLSI surface, so that the CCD sensors detect a diminished light quantity in the area where the labeled agent has bound. The method may also be used with fluorescent labels, making use of the fact that such labels absorb light at the excitation frequency. Alternatively, the CCD sensors may be used to detect the emission of the fluorescent label, after excitation. Separation of the emission signal from the excitation light may be achieved either by using sensors with different sensitivities for the different wavelengths, or by temporal resolution, or a combination of both.

In some embodiments, the method further includes acquiring one or more images of the first saccharide-binding agent and the saccharide-binding agent. The information can be is stored, e.g., as a photograph or digitized image. Alternatively, the information provided by the first and second binding image can be stored in a database.

The invention also includes a substrate that includes a plurality of complexes. Each complex includes a first saccharide-binding agent bound to a predetermined location on the substrate. The substrate can also optionally include a saccharide bound to the first saccharide-binding agent and/or a detectable second saccharide-binding agent. In some embodiments, the substrate is provided in the form of a solid support that includes in a pre-defined order a plurality of visual or otherwise detectable markers representative of a saccharide or saccharide sequence or fragment.

If desired, a substrate containing a plurality of first saccharide-binding agents can be provided in the form of a kit. Diagnostic procedures using the methods of this invention may be performed by diagnostic laboratories, experimental laboratories, practitioners, or private individuals. This invention provides diagnostic kits which can be used in these settings. The presence or absence of a particular carbohydrate polymer, as revealed by its pattern of reacting with saccharide binding agent, may be manifest in a provide sample. The sample can be, e.g., clinical sample obtained from that an individual or other sample.

Each kit necessarily comprises saccharide-binding agent or agents which renders the procedure specific. The reagent is preferably supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

The kit may optionally include a detectable second saccharide-binding agent and, if desired, reagents of detecting the second binding agent. The plurality of first saccharide-binding agents are preferably attached at predetermined location on the substrate and a detectable second saccharide-binding agent. In other embodiments, the kit is provided with a substrate and first saccharide-binding agents that can be attached to the substrate, as well as second saccharide-binding agents.

Generating Fingerprints of Carbohydrate Polymers

The method and reagents described above can be used to generate a fingerprint of a carbohydrate polymer. As used herein, a fingerprint of a carbohydrate polymer is a compilation of information about the binding status of the carbohydrate polymer and a plurality of scattered-binding agents. In some embodiments, the fingerprint is a numeric representation of the detection of the presence of binding by the saccharide-binding agents to the carbohydrate polymer.

The fingerprint of the carbohydrate polymer can be generated by contacting the carbohydrate polymer with a first saccharide-binding agent and determining whether the carbohydrate polymer binds to the saccharide-binding reagent. The carbohydrate polymer is also contacted with a second saccharide-binding agent, and a determination is made as to whether the second binding-agent binds to the carbohydrate polymer.

The carbohydrate polymer is preferably contacted with at least five saccharide-binding agents, and a determination is made as to whether the carbohydrate polymer binds to each of the at least five saccharide-binding reagents. In preferred embodiments, the binding of the carbohydrate polymer to at least 10, 15, 20, or 25 or more agents is determined.

In preferred embodiments, binding of the first and second saccharide-agent is determined by providing a surface comprising at least one first saccharide-binding agent attached to a predetermined location on the surface and contacting the surface with a carbohydrate polymer under conditions allowing for the formation of a first complex between the first saccharide-binding agent and the carbohydrate polymer. Unbound polymer is removed if desired and the surface is contacted with at least one second saccharide-binding agent under conditions allowing for formation of a second complex between the first complex and the second saccharide-binding agent. The first and second saccharide-binding agent are then identified, and the information generated provides a fingerprint for the carbohydrate polymer. By including a plurality of first and/or second saccharide-binding agents, it is possible to generate a detailed fingerprint of the carbohydrate polymer. Of course, it will be apparent to one of ordinary skill in the art that the absence of binding of a first or second saccharide-agent to a carbohydrate polymer will also contribute to the fingerprint generated for the polysaccharide.

The second saccharide agent preferably contains a detectable label. When the second saccharide-binding agent is labeled the identity of the second label determines the identity of the second saccharide-binding agent. The position of the second label on the substrate in turn reveals the identity of the first saccharide-binding agent.

The invention will be further illustrated in the following examples, which do not limit the scope of the appended claims.

EXAMPLE 1

Glycomolecule Analysis Using Antibodies as First and Second Sequence-Specific Agents This example further illustrates the technique of analyzing glycomolecules according to the invention. As a first and second sequence-specific agent antibodies are used. The following tables lists the results of reactions with two different saccharides denoted for purposes of illustration, HS and NS.

The structure of the sugars is as follows:

MFLNH-II (HS):

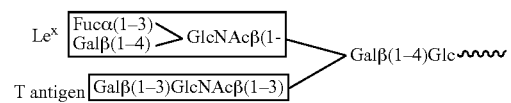

NS:

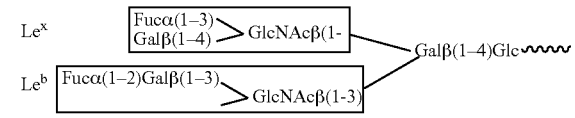

Table 2 lists the results of the reaction between the saccharide and the first and second essentially sequence-specific agents, which are antibodies against T-antigen, Lewis$^x$ (Le$^x$), or Lewis$^b$ antigen (Le$^b$). The first essentially sequence-specific agent is immobilized on a matrix, preferably a solid phase microparticle. The second essentially sequence-specific agent is labeled with a fluorescent agent, i.e., nile-red or green color. In addition, the reducing end of the saccharide is labeled, using a label clearly distinguishable from the nile-red or green color label which act as markers for the second essentially sequence-specific agents. Table 2 lists the reactions for the saccharide HS, while Table 3 lists the reactions for the saccharide NS.

TABLE 2

| On the matrix | anti T-antigen | Anti - Le$^x$ | anti - Le$^b$ |
|---|---|---|---|
| Saccharide bound | HS | HS | |
| Second mAb | nile-red anti - Le$^x$ | | |
| Signal | nile-red, reducing end | Reducing end | none |

TABLE 3

| On the matrix | anti T-antigen | Anti - Le$^x$ | anti - Le$^b$ |
|---|---|---|---|
| Saccharide bound | | NS | NS |
| Second mAb | | Green anti-Le$^b$ | nile-red anti - Le$^x$ |
| Signal | | Green, reducing end | nile-red, reducing end |

In summary, the following signals are now detectable in the reactions of the saccharide HS or NS (rows) when using the indicated antibodies as first essentially sequence-specific agent (columns):

TABLE 4

| On the matrix | anti T-antigen | Anti - Le$^x$ | anti - Le$^b$ |
|---|---|---|---|
| HS | nile-red, reducing end | Reducing end | |
| NS | | Green, reducing end | nile-red, reducing end |
| NS | | Green, reducing end | nile red, reducing end |

After the label has been detected and the result recorded for each reaction, a third essentially sequence-specific agent is added. In this example, two independent reactions with a third essentially sequence-specific agent are used. The solid phase carrying the sugar molecule may now be advantageously divided into aliquots, for reaction with either α1-2 Fucosidase or Exo β galactosidase (third essentially sequence-specific agents). Alternatively, three sets of reactions with a first and second essentially sequence-specific agent may be carried out.

TABLE 5 reactions after applying α1-3,4 Fucosidase:

| On the matrix | anti T-antigen | Anti - Le$^x$ | anti - Le$^b$ |
|---|---|---|---|
| HS | reducing end | | |
| NS | | | |

TABLE 6 reaction after applying Exo β galactosidase from D. pneumoniae (EC 3.2.1.23 catalog number 1088718 from Boehringer Mannheim, 68298 Mannheim, Germany)

| On the matrix | anti T-antigen | Anti - Le$^x$ | anti - Le$^b$ |
|---|---|---|---|
| HS | nile-red | | |
| NS | | Green | nile-red |

TABLE 7 reactions after applying α1-2 Fucosidase:

| On the matrix | anti T-antigen | Anti - Le$^x$ | anti - Le$^b$ |
|---|---|---|---|
| HS | nile-red, reducing end | Reducing end | |
| NS | | | Reducing end |

From the data gathered as explained above, a glycomolecule identity (GMID) card can now be created. An example for such information is listed in Table 8 for saccharide HS and in Table 9 for saccharide NS.

TABLE 8

| On the matrix | anti T-antigen | Anti - Le$^x$ | anti - Le$^b$ |
|---|---|---|---|
| 0 | nile-red, reducing end | Reducing end | |
| 1 | reducing end | — | — |
| 2 | nile-red | | |
| 3 | nile-red, reducing end | Reducing end | |

TABLE 9

| On the matrix | anti T-antigen | Anti - Le$^x$ | anti - Le$^b$ |
|---|---|---|---|
| 0 | | Green, reducing end | nile red, reducing end |
| 1 | — | — | — |
| 2 | | Green | nile red |
| 3 | | Reducing end | |

The identity of the second and third essentially sequence-specific agents need not be disclosed in such a data list. For the purpose of comparison, it is sufficient that a certain code number (1, 2 or 3 in the above tables) always identifies a certain combination of reagents.

EXAMPLE 2

A Scheme for the Sequential Labeling of Reducing Ends

As has been indicated in the description and example above, the method of the invention advantageously uses labeling of the saccharide to be investigated at its reducing end. However, this labeling technique may be extended to sites within the saccharide, and thus contribute to the method of the invention, by providing more information. As it is possible to label the saccharide within the chain, by cleavage using an endoglycosidase followed by labeling of the reducing end, it is therefore possible to obtain a labeled reducing end within the saccharide chain. As that reducing end is necessarily closer to the binding sites for the first, second and third essentially sequence-specific agents, compared to the original reducing end, the use of an internally created labeled reducing end provides additional information. Moreover, it is possible, by sequentially labeling of reducing ends according to the method described further below, to identify the sites for distinct glycosidases in sequential order on the chain of the saccharide to be investigated.

The method of sequential labeling of reducing ends is now described in more detail in the following steps:

1. Blocking:

A polysaccharide having a reducing end is incubated in a solution containing $NaBH_4/NaOH$ at pH 11.5.

This treatment blocks the reducing end, so that the polysaccharide is now devoid of a reducing end (RE).

2. Exposing:

The polysaccharide of step 1 is treated with an endoglycosidase. If the recognition site for that endoglycosidase is present within the polysaccharide, a new reducing end will be created by cleavage of the polysaccharide. The solution now contains two saccharides: the fragment with the newly exposed RE in the endoglycosidase site, and the second fragment whose RE is blocked.

3. Labeling of the Reducing End

This reaction may be carried out using e.g., 2-aminobenzamide (commercially available in kit form for labeling saccharides by Oxford Glycosystems Inc., 1994 catalog, p. 62). After the reaction under conditions of high concentrations of hydrogen and in high temperature (H+/T), followed by reduction, has been completed, the mixture contains two fragments, one of which is labeled at its reducing end, while the other remains unlabeled due to the fact that its reducing end is blocked.

Another way to label reducing ends is by reductive amination. Fluorescent compounds containing arylarnine groups are reacted with the aldehyde functionality of the reducing end. The resulting CH=N double bond is then reduced to a $CH_2$—N single bond, e.g., using sodium borohydride. This technology is part of the FACE (Fluorophore assisted Carbohydrate Electrophoresis) kit available from Glyko Inc., Novato, Calif., USA, as detailed e.g., in the Glyko, Inc. catalog, p. 8-13, which is incorporated herein by reference.

4. Reaction with a Second Endoglycosidase

A second endoglycosidase may now be reacted with the saccharide mixture. The new reaction mixture has now three fragments, one with an intact reducing end, a second with a reducing end labeled by 2-aminobenzimide, and a third with a blocked reducing end.

EXAMPLE 3

Derivation of Structural Information from a Series of Reactions with Essentially Sequence-Specific Agents This example further illustrates the method of the invention, i e., the generation of data related to the structure of the saccharide by using a set of reactions as described further above. The example further demonstrates that sequence information can be deduced from said set of reactions.

In some cases, the reagents used may not react exactly as predicted from published data, e.g. taken from catalogs. For instance, the lectin Datura stramonium agglutinin as described further below is listed in the Sigma catalog as binding GlcNac. However, in the reactions detailed further below, DSA is shown to bind to Coumarin 120-derivatized Glc (Glc-AMC). It appears that Glc-AMC acts like GlcNac for all purposes, because of the structural similarity between these compounds. Further, as apparent from the results below, the endogalactosidase used cleaves not only at galactose residues, but also the bond connecting the Glc-AMC group to the rest of the saccharide.

It is apparent that the essentially sequence-specific agents used in the practice of the invention may in some cases have fine specificities that vary from the specificity of these agents given in published material, e.g., catalogs. Such reactions can quickly be identified by using the method of the invention with saccharides of known structure. The results found may then be compared with expected results. and the differences will allow the identification of variant specificities of the essentially sequence-specific agents used. Such variation from published data in fine specificities of essentially sequence-specific agents may then be stored for future analysis of unknown saccharides structures using these agents.

In the following, the method of the invention is illustrated using an end-labeled pentasaccharide and various lectins and glycosidases. The pentasaccharide has the structure Gal-β(1,4)[Fuc-α(1,3)]-GlcNAc-β(1,3)-Galβ(1,4)-Glc. The pentasaccharide is branched at The GlcNAc position having fucose and galactose bound to it in positions 3 and 4 respectively. The pentasaccharide is labeled at its reducing end (Glc) with Coumarin-120 (7-amino-4-methyl coumarin, available, e.g., from Sigma, catalog No. A 9891). The coupling reaction may be carried out as described above for the labeling of reducing ends by using arylamine functionalities. Coumarin-120, when excited at 312 nm emits blue fluorescence. As first and second essentially sequence-specific agents, Endo-β-Galactosidase (EG, Boehringer Mannheim) and Exo-1,3-Fucosidase (FD, New England Biolabs) are used. The reaction conditions for both reagents are as described in the NEB catalogue for Exo-1,3-Fucosidase.

Three reactions were carried out. The first included Fucosidase (FD) and Endo-Galactosidase (EG), the second, FD only, and the third, EG only. A fourth reaction devoid of enzyme served as control.

In order to ascertain that the enzymes had digested the saccharide, the various reactions are size-separated using thin-layer chromatography (TLC).

After separation, the saccharides on the TLC plate may detected by exposing the plate to ultraviolet light. The results are shown in the following illustration.

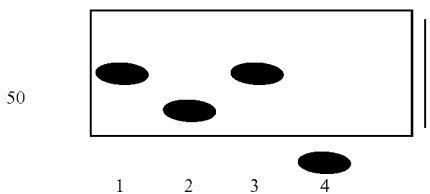

In reaction 4, no glycosidase was added. so the saccharide is intact and moves only a small distance on the plate. The fragment of reaction 2 is second in molecular weight, while the fragments of reactions 1 and 3 appear to be equal. From these data, it can be concluded that the sequence of the glycosidase sites on the saccharide is FD—EG—reducing end (coumarin-label).

The above pentasaccharide is now tested by a set of reactions as described further above. As first and second essentially sequence-specific agents, lectins were used. The lectins (Anguilla Anguilla agglutinin (AAA), catalog No. L4141, Arachis Fiypogaea agglutinin (PNA), catalog No. L0881, Ricinus communis agglutinin (RCA I) catalog No. L9138, Lens Culinaris agglutinin (LCA) catalog No. L9267, Arabs Precatorius agglutinin, (APA). catalog No. L9758) are available from Sigma. Lectins are also available from other companies. For instance, RCA I may be obtained from Pierce, catalog No. 39913. Lectins are immobilized by blotting onto nitrocellulose filters.

The reaction buffer is phosphate-buffered saline (PBS) with 1 mM CaCl and 1 mM MgCl. After binding of the lectins, the filter was blocked with 1% BSA in reaction buffer. As controls, reactions without lectin and with 10 μg BSA as immobilized protein were used.

The results of the reactions are indicated in Table 10. A plus indicates the presence of 312 nm fluorescence, which indicates the presence of the coumarin-labeled reducing end. The numerals 1-4 in the table indicate reactions as defined above.

TABLE 10

|   | AAA | PNA | LCA | DSA | RCA I |
|---|-----|-----|-----|-----|-------|
| 1 |     |     |     | ++  |       |
| 2 |     | ++  |     | ++  | ++    |
| 3 |     |     |     | ++  |       |
| 4 | ++  | ++  |     | ++  | ++    |

From the results as listed in Table 10 (reaction 4-control) it is evident that lectins AAA, PNA, DSA and RCA-I bind the saccharide. Therefore, Fucose, Gal(1-3)GlcNAc, GcNAc, and Galactose/GalNAc must be present in the saccharide, as these are the respective saccharide structures that are recognized by AAA, PNA, DSA and RCA-I. It is further evident that the above described glycosidases Fucosidase and Endo-β-Galactosidase recognize cleavage sequences in the saccharide. These sequences are Fuc (1-3/1-4) GlcNAc and GlcNAcβ(1-3)Galβ(1-3/4)Glc/GlcNAc, respectively.

It can further be deduced that both glycosidase sites are located between the fucose sugar and the reducing end, as said end is cleaved by either glycosidase when AAA (which binds to fucose) is used as immobilized lectin. The reaction with DSA, on the other hand, allows the deduction that either the GlcNAc monosaccharide is located between the glycosidase sites and the reducing end, or that Glc is directly bound to the coumarin, as neither glycosidase cleaves off the reducing end when DSA is used as immobilized agent.

Moreover, the reaction with PNA as immobilized agent shows that the reducing end is cleaved only if Endo-βGalactosidase is used (reactions 1 and 3). This indicates that the Endo-βGalactosidase site is located between the site for PNA and the reducing end. On the other hand, the Fucosidase site must be located between the PNA site and the other end of the saccharide.

When taking into account the above data, it is now possible to propose a sequence of the saccharide as follows:

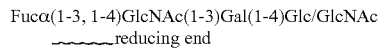

Fucα(1-3, 1-4)GlcNAc(1-3)Gal(1-4)Glc/GlcNAc
reducing end

The above experiment clearly demonstrates that the method of the invention can yield a variety of data, including sequence information, based upon relatively few reactions. Some details in the sequence information may not be complete, such as the (1-3) or (1-4) connection between Fucose and GlcNAc in the above saccharide. Had the monosaccharide composition of the pentasaccharide been known, then the above analysis would have yielded all of the details of said pentasaccharide. Nevertheless, the information gained even in the absence of the monosaccharide composition data is very precise compared to prior art methods.

EXAMPLE 4

Derivation of Partial or Complete Sequence Information

The method of the invention is suitable for automation. Thus, the steps described above, for example, in examples 1 to 3, may be carried out using an automated system for mixing, aliquoting, reacting, and detection. The data obtained by such an automated process may then be further processed in order to "collapse" the mapping information to partial or complete sequence information. The method for such data processing is described in further detail below.

After all data have been collected, a comparison is made between detection signals obtained from reactions prior to the addition of glycosidase, to signals obtained after the addition (and reaction with) of glycosidase. Those signals that disappear after reaction with glycosidase are marked. This may advantageously be done by preparing a list of those signals, referred to hereinafter as a first list. The identity of two sites on the polysaccharide may now be established for each such data entry. The position in the (optionally virtual) array indicates the first essentially sequence-specific agent. If a signal has been detected before reaction with the glycosidase, the recognition site for that agent must exist in the polysaccharide. The disappearance of a signal, for instance, of the signal associated with the second essentially sequence-specific agent, now indicates that the glycosidase cleaves between the recognition sites of the first and second essentially sequence-specific agents. The sequence of recognition sites is therefore (first essentially sequence-specific agent)-(glycosidase)-(second essentially sequence-specific agent). If the signal for the reducing end is still present after digestion with the glycosidase, then the relative order of the recognition sequences with respect to the reducing end can be established; otherwise, both possibilities (a-b-c and c-b-a) must be taken into account. For the purpose of illustration, the term "recognition site of the first essentially sequence-specific agent" shall be denoted in the following "first recognition site", the term "recognition site for the second essentially sequence-specific agent" shall be denoted "second recognition site", and the term "recognition site for glycosidase" shall be denoted "glycosidase".

It is now possible to create a second list of triplets of recognition sites of the above type (type 1 triplets):

(first recognition site)-(glycosidase)-(second recognition site).

Similarly, a third list can now be created relating to (optionally virtual) array locations where all signals remain after addition of glycosidase (type 2 triplets):

(glycosidase)-(first recognition site)-(second recognition site)

Obviously, a sufficient number of triplets defines a molecule in terms of its sequence, i.e., there can only be one sequence of saccharides that will contain all of the triplets found. A lower number of triplets may be required when information on the length of the molecule is available. The number of required triplets may be even lower if the total sugar content of the molecule is known. Both saccharide molecular weight and total monosaccharide content may be derived from prior art methods well known to the skilled person.

The process of obtaining sequence information, i.e., of collapsing the triplets into a map of recognition sites, is described below.

The second and third lists of triplet recognition sites are evaluated for identity (three out of three recognition sites identical), high similarity (two out of three recognition sites identical), and low similarity (one out of three recognition sites identical). For the purposes of illustration, it is now assumed that the polysaccharide is a linear polysaccharide, such as, for example, the saccharide portion of the glycan heparin.

The above second and third lists are then used to prepare therefrom a set of lists of triplets wherein each list in said set of lists contains triplets that share the same glycosidase recognition sequence. By comparing all triplets containing a certain glycosidase recognition sequence with all triplets containing a second glycosidase recognition sequence, it is now possible to divide the polysaccharide sequence into four areas, ranging from the first end of the molecule to glycosidase 1 (fragment a), from glycosidase 1 to glycosidase 2 (fragment b), and from glycosidase 2 to the second end of the molecule (fragment c):

<first end><glycosidase 1><glycosidase2><second end>

Identical recognition sites within triplets of type 2 with different glycosidase sites, wherein said recognition sites are located in the same direction in relation to the respective glycosidase site, are candidates for the location within either the area a or c, depending on said location. Identical recognition sites within triplets of type 2 with different glycosidase sites, wherein said recognition sites are located in different directions (e.g., one in the direction of the reducing end, in the other triplet, in the direction of the non-reducing end), are candidates for the location within the area b, i.e., between the two glycosidase sites.

Identical recognition sites within triplets of type 1 with different glycosidase sites are candidates for the location of one of the first or second recognition sites in area a (or c), and the other of said first or second recognition sites being located in the area c (or a). That is, if one of the first or second recognition sites is located in area a, then the other of said first or second recognition sites must be located in area b, and vice versa. None of the said first or second recognition sites may be located in area b.

Identical recognition sites within triplets of type 1 with different glycosidase sites, wherein a given recognition site is located in one of the triplets, in the direction of the reducing end and in the other triplet, in the direction of the non-reducing, are candidates for the location of said recognition site within area b.

Having established the above positional relationships for a number of recognition sites within the triplets, the total of the recognition sequences can now be arranged in a certain order using logical reasoning. This stage is referred to as a sequence map. If a sufficient number of recognition sequences are arranged, the full sequence of the saccharide may be derived therefrom. As the method does not determine the molecular weight of the saccharide, the chain length is unknown. Therefore, if the degree of overlap between the various recognition sites is insufficient, there may be regions in the sequence where additional saccharide units may be present. Such saccharide units may be undetected if they do not fall within a recognition site of any of the essentially sequence-specific agents used. However, the entire sequence information may also be obtained in this case, by first obtaining the molecular weight of the saccharide, which indicates its chain length, and secondly its total monosaccharide content.

Another possibility of closing gaps in the sequence map is the method of example 2, wherein sequential degradation by glycosidase is employed to derive sequence information.

The existence of branching points in the saccharide may complicate the method as outline above. One remedy to that is to use glycosidases to prepare fractions of the molecule, and analyze these partial structures. The extent of branching in such partial structures is obviously lower than in the entire molecule. In addition, reagents may be employed that specifically recognize branching points. Examples for such reagents are e.g., the antibodies employed in example 1 above. Each of these antibodies binds a saccharide sequence that contains at least one branching point. Moreover, certain enzymes and lectins are available that recognize branched saccharide structures. For instance, the enzyme pullanase (EC 3.2.1.41) recognizes a branched structure. In addition, antibodies may be generated by using branched saccharide structures as antigens. Moreover, it is possible to generate peptides that bind certain saccharide structures, including branched structures (see e.g., Deng S J, MacKenzie C R, Sadowska J, Michniewicz J, Young N M, Bundle D R, Narang; Selection of antibody single-chain variable fragments with improved carbohydrate binding by phage display. J. Biol. Chem. 269, 9533-38, 1994).

In addition, knowledge of the structure of existing carbohydrates will in many cases predict accurately the existence of branching points. For instance, N-linked glycans possess a limited number of structures, as listed at p. 6 of the oxford Glycosystems catalog. These structures range from monoantennary to pentaantennary. The more complicated structures resemble simpler structures with additional saccharide residues added. Therefore, if monoantennary structure is identified, it is possible to predict all of the branching points in a more complicated structure, simply by identifying the additional residues and comparing these data with a library of N-linked glycan structures.

Moreover, it will often be possible by analyzing data gathered according to the method of the invention, to deduce the existence and location of branching points logically. For instance, if two recognition sites, denoted a and b, are located on different branches, then digesting with a glycosidase whose site is located between the reducing end and the branching point will result in loss of the reducing end marker. The markers for both recognition sites a and b, however, will remain. If a glycosidase located between the branching point and recognition site a is used, then the marker for recognition site b and the reducing end marker will be cleaved off. Not taking into account the possibility of branching points, this would indicate that the recognition site b is located between the recognition site a and the reducing end. However, if a glycosidase located between the recognition site b and the branching point is used, the reducing end marker and recognition site a will be cleaved off. Again, not taking into account the possibility of branching, this would indicate that recognition site a is located between the reducing end and recognition site b. These deductions are obviously incompatible with one another, and can only be resolved if one assumes that recognition sites a and b are located on two different branches. The branching point is located between the recognition sites a and b and the first of the above glycosidases. The other above glycosidases used are located on a branch each, between the branching point and the respective recognition site (a or b).

Therefore, when using agents that recognize branched structures in the method of the invention, as essentially sequence-specific agents, it is possible to derive information on the existence and location of branching points in the saccharide molecule. This information can then be used to construct sequence maps of each branch of the structure, yielding a sequence map of the entire branched structure. The gaps in such a structure may then be closed as in the case of unbranched saccharides, according to the invention, i.e., by using additional reactions, by digestion with glycosidases, whereby the regions of the molecule where gaps exist are specifically isolated for further analysis according to the method of the invention, and by sequential glycosidase digestion as described further above.

In summary, a method for determining the sequence of a saccharide and/or for mapping the structure of said saccharide according to the invention comprises the steps of:
1. collecting triplets of type 1 and type 2
2. sorting said triplets according to similarity
3. comparing triplets with different glycosidase recognition sites
4. arranging the triplets in the order of occurrence on the saccharide
5. arranging the glycosidase recognition sites
6. checking the compatibility to the triplets
7. arranging recognition sequences of glycosidases and of first and second essentially sequence-specific agents in a single file order
8. translating the recognition sequences (sites) into polysaccharide sequence
9. correcting "overlap" problems
10. outputting a sequence
11. checking against all available data After the above step 5 has been carried out, a preliminary order of glycosidase sites has been established. In step 6, it is now checked for each triplet whether predictions based thereon are in agreement with that order. Then, based on contradiction in the data, a new model is generated that fits the data of the triplet. This model is then tested against the data of all triplets. Furthermore, additional reactions may be carried out, in order to extract additional vectorial information regarding the recognition sites that involve said triplet.

After the above step 8, wherein the sequentially arranged recognition sites are translated into a sequence of actual monosaccharide units, a model of the saccharide sequence can be suggested. In order to test said model, a number of questions needs to be answered. The first of these is, what is the minimum sequence that would still have the same sequence map? At this stage, information on molecular weight and monosaccharide composition, if available, is not taken into account. This approach merely serves the creation of a sequence which incorporates all of the available data with as few as possible contradictions. In that respect, the second question to be answered is, does the minimum sequence still agree with all of the data available at that point (excluding optional molecular weight and monosaccharide composition data)? The third question to be answered is, do other sequences exist that would fit the sequence map as established? In the affirmative, the additional sequences may then be tested using the question: How does each sequence model agree with the triplet information, and with additional optional data, such as information on the molecular weight, monosaccharide composition, and model saccharide structures known from biology.

Finally, the sequence model that has been found to be best according to the steps 1-10 described above, will then be tested against all triplets, monosaccharide composition, prior knowledge on the molecular weight and structural composition of the saccharide, and predictions from biologically existent similar structures. By such repeated testing, the contradictions between the available data and the sequence model are identified, and if possible, the sequence model is adapted to better represent the data.

EXAMPLE 5

Glycomolecule Identity (GMID) Analysis of Milk Samples

The aim of this example is to demonstrate the application of the GMID technique to the analysis and comparison of milk samples.

A. Membranes and 1$^{st}$ layer lectins:

The supporting surface used in the experiments described hereinbelow is a nitrocellulose membrane. The membranes were prepared as follows:
1. Nitrocellulose membranes were cut out and their top surface marked out into an array of 9×6 squares (3 mm$^2$ each square). The membranes were then placed on absorbent paper and the top left square of each one marked with a pen.
2. Lyophilized lectins were resuspended in water to a final concentration of 1 mg/ml. The resuspended lectins (and a control solution: 5% bovine serum albumin) were vortex mixed and 1 µl of each solution is added to one of the 28 squares on the blot, indicated by shading in the following illustrative representation of a typical blot:

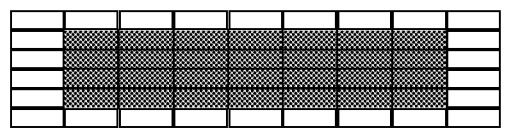

The lectins used in this experiment are listed in Table 11.

TABLE 11

| Lectin | Manufacturer | Cat. No. |
| --- | --- | --- |
| WGA | Vector | MK2000 |
| SBA | Vector | MK2000 |
| PNA | Vector | MK2000 |
| DBA | Vector | MK2000 |
| UEA I | Vector | MK2000 |
| CON A | Vector | MK2000 |
| RCA I | Vector | MK2000 |
| BSL I | Vector | MK3000 |
| SJA | Vector | MK3000 |
| LCA | Vector | MK3000 |
| Swga | Vector | MK3000 |
| PHA-L | Vector | MK3000 |
| PSA | Vector | MK3000 |
| AAA | — | — |
| PHA-E | Vector | MK3000 |
| PNA | Leuven | LE-408 |
| LCA | Sigma | L9267 |
| DSA | Sigma | L2766 |
| APA | — | — |
| WGA | Leuven | LE-429 |
| Jacalin | Leuven | LE-435 |
| 5% BSA | Savyon | M121-033 |

3. The prepared blots were placed in 90 mm petri dishes.
4. The blots were blocked by adding to each petri dish 10 ml of any suitable blocking solution well known to the skilled artisan (e.g. 5% bovine serine albumin).
5. The dishes containing the blots in the blocking solution were agitated gently by rotation on a rotating table (50 rpm) for 2 hours at room temperature (or overnight at 40° C., without rotation).

6. The blots were then washed by addition of 10 ml washing solution to each petri dish.

Any commonly available buffered solution (e.g. phosphate buffered saline) may be used for performing the washing steps. The dishes were washed by rotating gently (50 rpm) for 5 minutes. The procedure was performed a total of three times, discarding the old washing solution and replacing with fresh solution each time.

B: Addition of Milk Samples:

The milk samples used were as follows:
1. Bovine UHT long-life milk (3% fat) obtained from Ramat haGolan dairies, Israel (lot 522104);
2. Pasteurized goat's milk, obtained from Mechek dairies, Israel (lots 1 and 2);
3. Non-pasteurized goat's milked obtained as in 2. (lots 3 and 4).

The milk samples were diluted to 10% v/v and approximately 5 ml of each sample applied to separate blots.

Duplicate blots were prepared for each of the aforementioned milk samples. In addition a further pair of blots were prepared without the addition of saccharides (negative control).

The blots were then incubated at room temperature with agitation for one hour.

C. Colored Lectins:

From prior knowledge of the monosaccharide composition of the milks tested, and by application of a computer program based on the algorithm described hereinbelow in Example 7, the following colored lectins were chosen: Con A, VVA.

A mixture of these two lectins was prepared in washing solution, such that the concentration of each colored lectin was 2 mg/ml.

500 μl of each lectin mix was incubated on the blots prepared as described above. Each blot was read both by measuring the fluorescence of fluorescein at 520 nm, and, in the case of the biotinylated lectin, measuring the signal of the TMB blue color produced following reaction of biotin with an HRP-streptavidin solution The results obtained for the FITC-labeled and biotin-labeled lectins are given in Tables 12 and 13, respectively. The results presented in these tables are measured on a 0 to 3 scale, wherein 0 represents a signal that is below the noise level, and wherein results of 1-3 represent positive signals (above noise) following subtraction of the results obtained in the no-saccharide control.

Glycomolecule identity (GMID) cards obtained from these results for pasteurized goat's milk (lots 1 and 2), non-pasteurized goat's milk (lots 3 and 4) and bovine milk are shown in FIG. 1 (A to E, respectively). The positions of lectins 1 to 24 are shown in one row from left to right at the top of each card 1.

D. Interpretation of Results:

The bovine milk sample yielded a GMID indicating that the polysaccharide in the sample contains saccharides that yield positive results for lectins specific for:
a. glucose/mannose (ConA, PSA and LCA),
b. GlcNac (WGA and DSA).

The pasteurized goat milk samples yielded positive results for:
a. glucose/mannose (conA, PSA and LCA);
b. GlcNac (DSA).

No difference in lectin reactivity between the lots tested was observed.

The non-pasteurized goat milk sample gave a positive reaction for:
a. glucose/mannose (ConA, PSA and LCA),
b. GlcNac (DSA).

In summary, the bovine milk differed from the goat's milk in that only the former reacted with WGA. There was essentially no difference between the pasteurized and non-pasteurized goat's milk samples, with the exception that the signal intensity was significantly lower in the pasteurized samples.

EXAMPLE 6

Glycomolecule Identity (GMID) Analysis of Lipopolysaccharides

A GMID analysis was performed on five different bacterial lipopolysaccharides obtained from Sigma Chemical Co. (St. Louis, Mo., USA)(LPS#1, 7, 10, 15 and 16), essentially using the method as described in Example 5, above. The colored lectins used were ECL, WGA, VVA and SBA.

The GMID cards obtained for samples LPS# 1, 7, 10, 15 and 16 are shown in FIG. 2 (A to E, respectively). It may be seen from this figure that the GMID cards provide unique "fingerprints" for each of the different lipopolysaccharides, and may be used for identifying the presence of these compounds in samples containing bacteria or mixtures of their products.

EXAMPLE 7

Method for Selecting Colored Lectins

Figure 3:
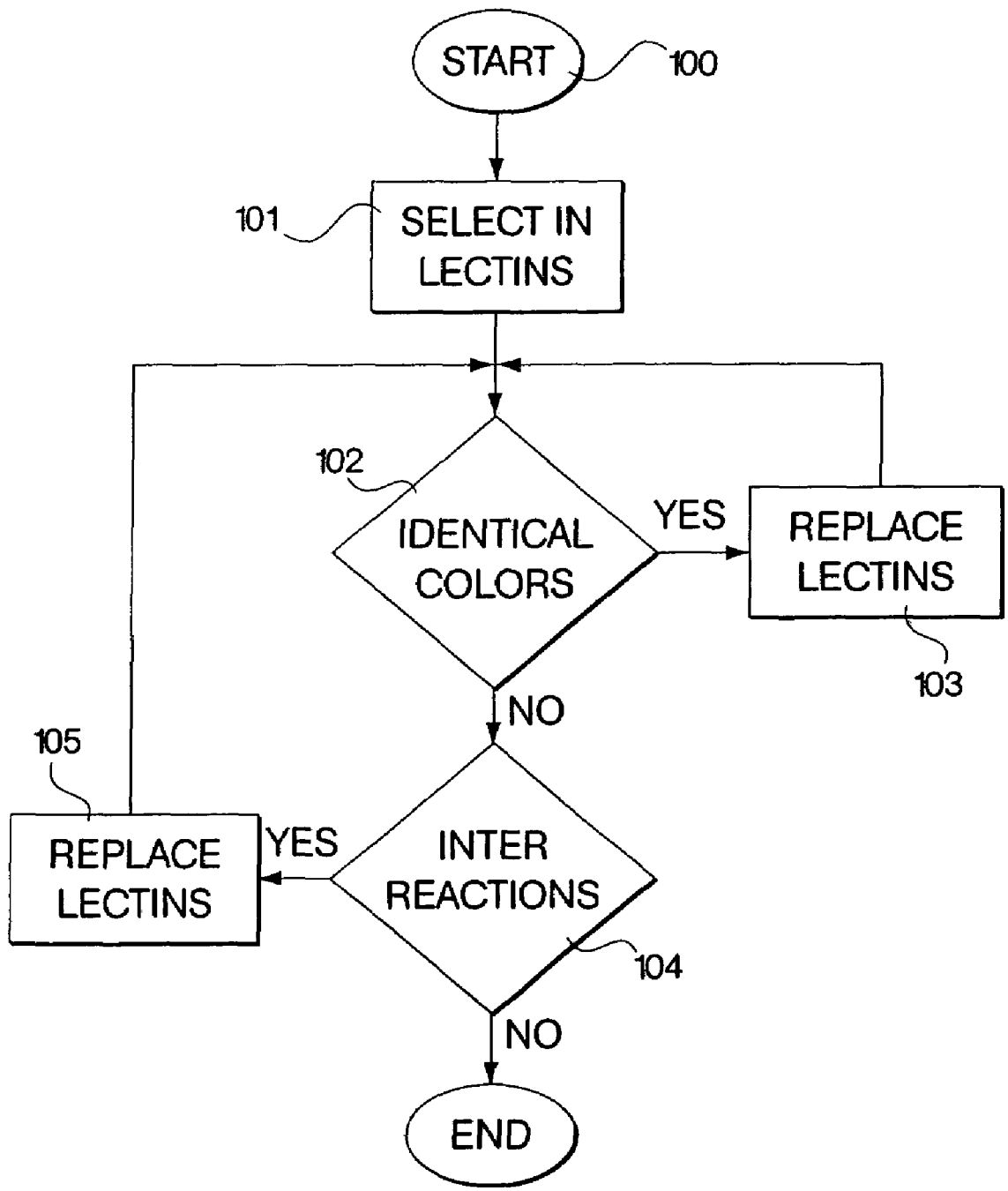
FIG. 3 is a high-level logic flowchart that illustrates an algorithm for choosing a set of colored lectins.

A number of factors must be taken into consideration when selecting colored lectins for use in the method of polysaccharide analysis illustrated in Examples 5 and 6. Among these considerations are the need for each of the chosen lectins to have a distinguishable color or other detectable marker, and for the need to reduce interactions between lectins. A flow chart illustrating an algorithm for use in colored marker selection is shown in FIG. 3. The algorithm shown in FIG. 3 begins with the selection of n colored lectins (or other detectable markers) 101, said initial selection being made in accordance with information obtained about the partial or full monosaccharide composition of the saccharide to be analyzed.

In the next step 102, the colors of the selected lectins are examined in order to check for identity/non-identity of the colors selected. If there are identical colors in the selected group, then the process proceeds to step 103, otherwise the flow proceeds with step 104. In step 103, one of the lectins that has been found to have a non-unique color is replaced by another lectin that belongs to the same binding category (that is, one that has the same monosaccharide binding specificity); the flow proceeds to step 102.

In step 104, the n selected lectins are tested in order to detect any cross-reactivity with each other, and with the non-colored lectins used in the first stage of the method described hereinabove in Example 5. If cross-reactivity is found, then the process continues to step 105, otherwise the flow proceeds to step 106, where the algorithm ends.

In step 105, one of the lectins determined to cross-react with another lectin is replaced by a lectin which does not cross-react; the flow then proceeds to 102. The algorithm ends with step 106.

It is to be emphasized that while for values of n which are small, and for saccharides with a simple monosaccharide composition, the above-described algorithm may be applied by the operator himself/herself manually working through each step of the selection procedure. Alternatively (and especially for cases where n is a larger number or the monosaccharide composition is more complex), the algorithmic processes described hereinabove may be performed by a computer program designed to execute said processes.

The above examples have demonstrated the usefulness of the method described herein. However, they have been added for the purpose of illustration only. It is clear to the skilled person that many variations in the essentially sequence-specific agents used, in the reaction conditions therefor, in the technique of immobilization, and in the sequence of labeling, reaction and detection steps may be effected, all without exceeding the scope of the invention.

Other Embodiments

Figure 4:
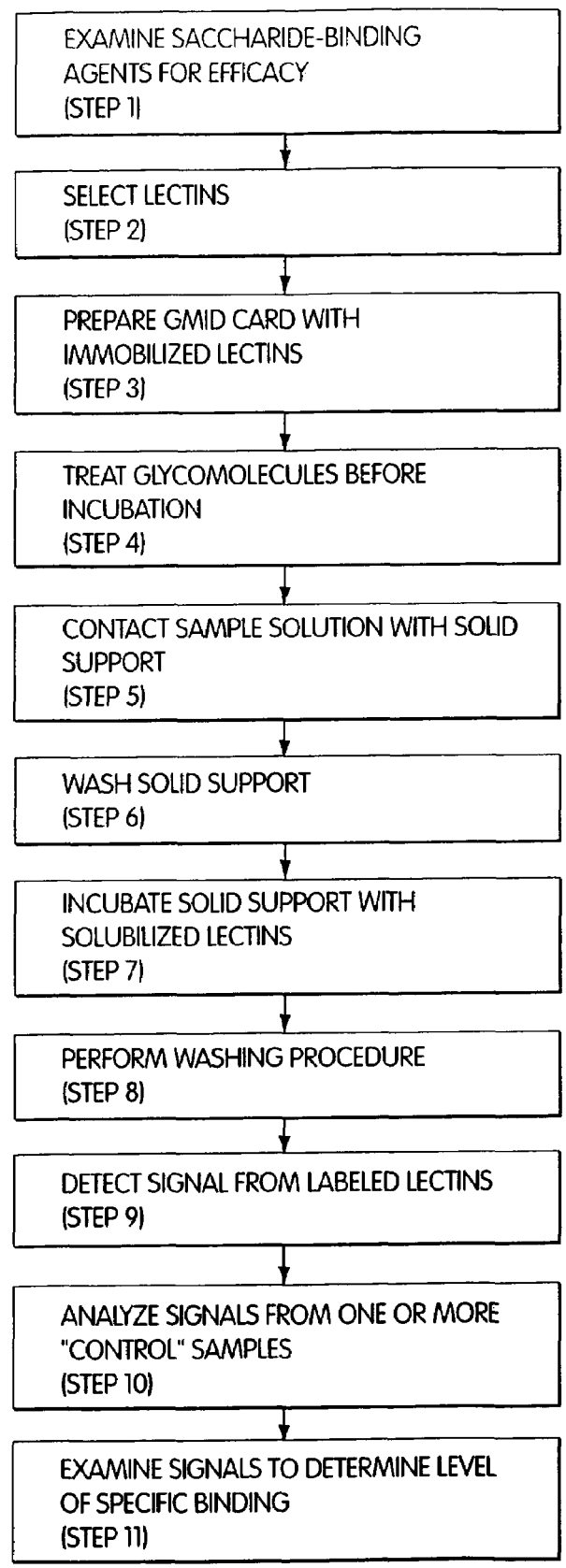
FIG. 4 is a flowchart of an exemplary method according to the present invention for performing a fingerprint assay with a GMID card.

The above Examples describe particular types of fingerprint assays and methods according to the present invention. These assays may optionally be performed with a variety of different configurations for "wet" or experimental assay devices, hardware and software programs for gathering and analyzing the data. FIG. 4 is a schematic block diagram of an exemplary method according to the present invention for performing a fingerprint assay with the GMID card, which illustrates one type of systemic configuration and operation according to the present invention for performing the fingerprint assay. It should be noted that this description is intended as an example only and is not meant to be limiting in any way.

As shown, in step 1, optionally and preferably, the saccharide-binding agents are examined for efficacy before they are used in the assay with the GMID card. In this example, the saccharide-binding agents are described as lectins, although of course other such agents could optionally be used within the scope of the present invention. More preferably, each such lectin is examined for positive activity, most preferably through reactivity with a standard glycomolecule. Such reactivity shows that the lectin is capable of binding to such a standard glycomolecule in a reproducible manner. Additionally and also preferably, the lectin should be tested for its ability to operate as either saccharide-binding agent in the preferred embodiment of the assay, whether attached to the surface of the solid support, or alternatively present in a solubilized form.

In step 2, the lectins are optionally and preferably examined for their ability to bind to the solid support for the GMID card for the immobilized saccharide-binding agent. In addition, optionally and preferably, the solubilized form of the saccharide-binding agents is examined in order to determine if there is any non-specific binding to the solid support, which may increase levels of background lectin binding, thereby degrading the signal of the specifically bound lectins.

In addition, more preferably the solid support for the GMID card is itself examined for various types of behaviors, such as generation of background signals in the absence of specific lectin binding, and/or quenching of such signals. A particularly preferred solid support for the GMID card of the present invention is a porous or semi-porous membrane, such as nitrocellulose for example. Alternatively, the solid support could be a nitrocellulose coated solid surface such as a glass slide, for example, or any other suitable solid surface which has been coated with a porous or semi-porous material.

In step 3, once the set of lectins has been selected for immobilization on the solid support for the GMID card, and the support itself has also been selected, then the GMID card is prepared with the immobilized lectins. Optionally, the GMID card may be prepared with "arrayer" or "spotting" devices, which are able to place relatively small, precise amounts of lectins in a specific array on the solid support, to form an array of a plurality of "spots". These devices are also known as "microdispensing systems", as they deposit volumes of material which are typically measured in nanoliters, for example with an array of pins for depositing such small volumes of material. Examples of suitable devices which are operative with the present invention include, but are not limited to, Hydra™ (Robbins Inc., USA), MicroGrid II/TAS/Pro™ (BioRobotics Ltd., United Kingdom) and GMS417™ (Genetic Microsystems Affymetrix Inc., USA).

Optionally and preferably, the lectins are pretreated before being immobilized to the solid surface or incubated with the GMID card in the solubilized form. For example, such pretreatment could optionally include periodation of the lectins in order to improve the signal to noise ratio.

In step 4, optionally and more preferably, before being incubated with the GMID card, the glycomolecules are treated to maximize the efficiency of specific binding to the immobilized lectins on the support, and also to decrease non-specific binding to the immobilized lectins, the support and the solubilized lectins. In addition, preferably the glycomolecules are mixed with an appropriate buffer in order to form the sample solution.

In step 5, the sample solution is contacted with the solid support containing the immobilized lectins. Optionally, before the sample solution is contacted with the solid support, the solid support is washed with the sample buffer alone. The sample solution with the glycomolecules is then incubated with the solid support for an appropriate period of time. Optionally, a control solution is also incubated with at least a portion of the solid support,. as a measurement for non-specific binding.

In step 6, the solid support with the complexed glycomolecules is then preferably washed at least once with an appropriate washing buffer, as well as with an appropriate blocking buffer. In step 7, the solid support is then incubated with the solubilized, labeled lectins as the second saccharide-binding agent. In step 8, again an appropriate washing procedure is preferably performed.

In step 9, the signal from the labeled lectins is detected with an appropriate detection device. For example, if the label is chromogenic, then the detection device could be a CCD (charge-coupled device) camera. Clearly, one of ordinary skill in the art could select the appropriate detection device according to the type of label on the lectin.

According to preferred embodiments of the present invention, the label is a fluorescent dye, as previously described. For such a preferred embodiment, the detection device would also preferably include a light source of an appropriate wave length, for exciting the fluorescent dye label, and also an appropriate filter set for optionally filtering the light from the light source and for filtering the resultant signal. It should be noted that such filters are not required for monochromatic light sources, such as lasers for example. The possibility of photobleaching and the efficiency cofactor of each dye or fluorochrome is preferably considered in the analysis phase, as described in greater detail below.

The image of the entirety or at least a significant majority of the GMID card could optionally be obtained (as opposed to the detection of a plurality of single signals, for example). Examples of suitable detection devices include "scanners" for obtaining at least a portion of the image of the GMID card, with multiple signals from a plurality of "spots". Such devices may optionally be single band (light of a single wavelength is detected); double band (light of two separate wavelengths is detected); or spectrum devices (light is detected of at least two, but preferably a large number of, wavelengths).

In step 10, most preferably, the various signals from one or more control "samples" are analyzed in order to determine the appropriate threshold for the signal for the specifically bound lectins, as well as for determining signal to noise ratios, and so forth. In addition, these various signals can optionally be compared to the results from previous assays, in order to verify the quality of the assay for example.

In step 11, optionally and preferably the signals are examined in order to determine the level of specific binding, if any, for example by subtraction of background noise and by comparison to the threshold for specifically bound lectins. The background noise is preferably determined as a function of the average noise, ± the standard deviation.

Steps 9-11 are optionally and preferably performed with a software program for controlling the process of capturing the signal, for example in the form of image data; analyzing the control signals; and then analyzing the sample signals in order to obtain the actual assay data. Examples of suitable software programs include, but are not limited to, Gene-Tools™ (BioRobotics Ltd., United Kingdom); GenePix Pro 3.0™ (Axon Instruments Inc.) and QuantArray™ (GSI Lumonics Inc.). Alternatively, these steps could be optionally performed with firmware and/or hardware, or some combination thereof.

According to preferred embodiments of the present invention, these steps preferably include the step of first defining the array for the "spots". Such an array is optionally and more preferably defined automatically, and includes the definition of a grid for determining the expected location of any specific signal from the "spots". Next, the initial location of the spots is preferably determined in relation to the grid. Each individual spot is then centered, after which edge detection is preferably performed to locate the boundary of each spot. Edge detection is optionally performed according to a free form determination of the size and shape of the spots; a fixed form determination for the size and shape; or alternatively a fixed size but free shape determination process. Any of these steps may be performed automatically or alternatively may be performed manually.

Next, the intensity of the signal for each spot is determined. Such an intensity is preferably determined relative to the background signal and to the signal to noise ratio, for example by subtracting the background signal from the raw signal data which is detected by the detection device.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for characterizing a carbohydrate polymer, the method comprising:
   a) providing a surface comprising a plurality of different essentially sequence- and/or site-specific binding agents having different binding specificities attached to a plurality of predetermined locations on said surface;
   b) contacting said surface with a carbohydrate polymer sample;
   c) contacting said surface with at least one saccharide-binding agent, wherein at least one of the carbohydrate polymer sample or saccharide-binding agent comprise a detectable label;
   d) detecting said label; and
   e) identifying said saccharide-binding agent if bound in a complex with said carbohydrate polymer and if said carbohydrate polymer is bound in a complex with at least one of a plurality of different essentially sequence- and/or site-specific binding agents,
   thereby characterizing said carbohydrate polymer.

2. The method of claim 1, wherein said at least one of said plurality of different essentially sequence- and/or site-specific binding agents is identified by determining the location of the detected label on the substrate.

3. The method of claim 2, wherein said detectable label is selected from the group consisting of a chromogenic labels, a radiolabel, a fluorescent label, and a biotinylated label.

4. The method of claim 1, wherein said surface comprises at least five different essentially sequence- and/or site-specific binding agents affixed to said surface.

5. The method of claim 1, wherein said surface comprises at least 15 different essentially sequence- and/or site-specific binding agents affixed to said surface.

6. The method of claim 1, wherein said surface is contacted with at least 5 different saccharide-binding agents.

7. The method of claim 1, wherein said surface is contacted with at least 15 different saccharide-binding agents.

8. The method of claim 4, wherein said surface is contacted with at least five different saccharide-binding agents.

9. The method of claim 5, wherein said surface is contacted with at least 15 different saccharide-binding agents.

10. The method of claim 6, wherein said plurality of different essentially sequence- and/or site-specific binding agents is selected from the group consisting of a lectin, a saccharide-cleaving enzyme, and an antibody.

11. The method of claim 7, wherein said saccharide binding agent is selected from the group consisting of a lectin, a polysaccharide-cleaving enzyme, a saccharide modifying enzyme, and an antibody to a saccharide.

12. The method of claim 10, wherein said saccharide binding agent is selected from the group consisting of a lectin, a polysaccharide-cleaving or modifying enzyme, and an antibody to a saccharide.

13. The method of claim 11, wherein said carbohydrate polymer is provided after digestion with a saccharide-cleaving agent.

14. The method of claim 1, wherein said carbohydrate polymer is digested with a saccharide-cleaving agent prior to contacting said saccharide with said saccharide-binding agent.

15. The method of claim 1, further comprising removing unbound plurality of different essentially sequence- and/or site-specific binding agents from said surface prior to contacting said surface with said saccharide-binding agent.

16. The method of claim 1, wherein said method further comprises acquiring one or more images of said plurality of different essentially sequence- and/or site-specific binding agents and said saccharide-binding agent.

17. The method of claim 16, wherein said image is stored.

18. The method of claim 17, wherein said image is stored as a photograph or digitized image.

19. A method of generating a fingerprint of a carbohydrate polymer, the method comprising
   providing a carbohydrate polymer sample,
   contacting said carbohydrate polymer with a plurality of different essentially sequence- and/or site-specific binding agents;
   determining whether said carbohydrate polymer binds to at least one of said plurality of different essentially sequence- and/or site-specific binding agents;
   contacting said carbohydrate polymer with a saccharide-binding agent, wherein at least one of the carbohydrate polymer sample or saccharide-binding agent comprise a detectable label;
   detecting said label; and
   determining whether said carbohydrate polymer binds to said saccharide-binding reagent, thereby generating a fingerprint of said carbohydrate polymer.

20. The method of claim 19, further comprising contacting said carbohydrate polymer with at least five different essentially sequence- and/or site-specific binding agents, and determining whether said carbohydrate polymer binds to each of said at least five different essentially sequence- and/or site-specific binding agents.

21. The method of claim 19, further comprising contacting said carbohydrate polymer with at least 15 different essentially sequence- and/or site-specific binding agents, and determining whether said carbohydrate polymer binds to each of said at least 15 different essentially sequence- and/or site-specific binding agents.

22. The method of claim 19, wherein said carbohydrate polymer is selected from the group consisting of a glycoprotein and a glycolipid.

23. The method of claim 19, wherein said carbohydrate polymer is a polysaccharide.

24. The method of claim 19, wherein binding of each of said plurality of different essentially sequence- and/or site-specific binding agents and said saccharide binding agent is determined by
a) providing a surface comprising a plurality of different essentially sequence- and/or site-specific binding agents having different binding specificities attached to a plurality of predetermined locations on said surface;
b) contacting said surface with a carbohydrate polymer sample;
c) contacting said surface with at least one saccharide-binding agent, wherein at least one of the carbohydrate polymer sample or saccharide-binding agent comprise a detectable label;
d) detecting said label; and
e) identifying said saccharide binding agent if bound in a complex with said carbohydrate polymer and if said carbohydrate polymer is bound in a complex with at least one of said plurality of different essentially sequence- and/or site-specific binding agents.

25. The method of claim 19, wherein said at least one of said plurality of different essentially sequence and/or site-specific binding agent is identified by determining the location of the detected label on the substrate.

26. The method of claim 19, wherein said detectable label is selected from the group consisting of a chromogenic label, a radiolabel, a fluorescent label, and a biotinylated label.

27. The method of claim 19, wherein said surface comprises at least five different essentially sequence and/or site-specific binding agents affixed to said surface.

28. The method of claim 19, wherein said surface comprises at least 15 different essentially sequence and/or site-specific binding agents affixed to said surface.

29. The method of claim 19, wherein said surface is contacted with at least 5 different saccharide-binding agents.

30. The method of claim 19, wherein said surface is contacted with at least 15 different saccharide-binding agents.

31. The method of claim 19, wherein said surface is contacted with at least five saccharide-binding agents.

32. The method of claim 19, wherein said surface is contacted with at least 15 different saccharide-binding agents.

33. The method of claim 19, wherein said plurality of different essentially sequence and/or site-specific binding agents is selected from the group consisting of a lectin, a saccharide-cleaving enzyme, and an antibody.

34. The method of claim 33, wherein said saccharide binding agent is selected from the group consisting of a lectin, a polysaccharide-cleaving or modifying enzyme, and an antibody to a saccharide.

35. The method of claim 19, wherein said saccharide binding agent is selected from the group consisting of a lectin, a polysaccharide-modifying or cleaving enzyme, and an antibody to a saccharide.

36. The method of claim 19, wherein said carbohydrate polymer is provided after digestion with a saccharide-cleaving agent.

37. The method of claim 19, wherein said carbohydrate polymer is digested with a saccharide-cleaving agent prior to contacting said saccharide with said saccharide-binding agent.

* * * * *